(12) United States Patent
Sajgalik et al.

(10) Patent No.: US 10,918,292 B2
(45) Date of Patent: Feb. 16, 2021

(54) NON-INVASIVE CARDIAC OUTPUT ASSESSMENT

(71) Applicant: Mayo Foundation for Medical Education and Research, Rochester, MN (US)

(72) Inventors: Pavol Sajgalik, Rochester, MN (US); Vaclav Kremen, Rochester, MN (US); Bruce D. Johnson, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 68 days.

(21) Appl. No.: 16/318,262

(22) PCT Filed: Jul. 18, 2017

(86) PCT No.: PCT/US2017/042533
§ 371 (c)(1),
(2) Date: Jan. 16, 2019

(87) PCT Pub. No.: WO2018/017542
PCT Pub. Date: Jan. 25, 2018

(65) Prior Publication Data
US 2019/0167121 A1 Jun. 6, 2019

Related U.S. Application Data

(60) Provisional application No. 62/364,155, filed on Jul. 19, 2016.

(51) Int. Cl.
*A61B 5/029* (2006.01)
*A61B 5/00* (2006.01)
(Continued)

(52) U.S. Cl.
CPC ............. *A61B 5/029* (2013.01); *A61B 5/02* (2013.01); *A61B 5/02108* (2013.01);
(Continued)

(58) Field of Classification Search
CPC .................................................. A61B 5/02225
See application file for complete search history.

(56) References Cited

U.S. PATENT DOCUMENTS 7,727,157 B2   5/2010 Sharrock
10,251,567 B2  4/2019 Fabian et al.
(Continued)

OTHER PUBLICATIONS

McGrath et al., "Pulse oximeter plethysmographic waveform changes in awake, spontaneously breathing, hypovolemic volunteers," Anesth Analg, Feb. 2011, 112(2): 368-374.
(Continued)

*Primary Examiner* — Rex R Holmes
*Assistant Examiner* — Jennifer L Ghand
(74) *Attorney, Agent, or Firm* — Fish & Richardson P.C.

(57) ABSTRACT

Non-invasive systems can be used to estimate cardiac output and stroke volume. For example, this document provides cuff occlusion systems and methods for their use so that cardiac output and stroke volume can be estimated in a non-invasive fashion. In some implementations, a patient's brachial artery is occluded by an inflatable cuff device for a period of time. A heart rate and a plurality of blood pressure pulse wave measurement curves can be measured using the cuff device. The data collected can be used to calculate an estimate of the patient's cardiac output and stroke volume.

15 Claims, 6 Drawing Sheets

(51) Int. Cl.
 A61B 5/021 (2006.01)
 A61B 5/022 (2006.01)
 A61B 5/02 (2006.01)
(52) U.S. Cl.
 CPC ........ *A61B 5/02225* (2013.01); *A61B 5/7203* (2013.01); *A61B 5/6824* (2013.01)

(56) References Cited

U.S. PATENT DOCUMENTS

| | | | |
|---|---|---|---|
| 2002/0022785 A1* | 2/2002 | Romano | A61B 5/029 600/526 |
| 2003/0040675 A1 | 2/2003 | Sharrock | |
| 2009/0287097 A1 | 11/2009 | Lowe | |
| 2010/0152593 A1 | 6/2010 | Lowe | |
| 2011/0040195 A1* | 2/2011 | Knoll | A61B 5/029 600/485 |
| 2014/0128747 A1 | 5/2014 | Maltz | |
| 2014/0135632 A1 | 5/2014 | Sharrock et al. | |

OTHER PUBLICATIONS

PCT International Search Report and Written Opinion in International Appln. No. PCT/US/2017/42533, dated Oct. 2, 2017, 12 pages.

\* cited by examiner

NON-INVASIVE CARDIAC OUTPUT ASSESSMENT

CROSS REFERENCE TO RELATED APPLICATIONS

This application is a National Stage application under 35 U.S.C. § 371 of International Application No. PCT/US2017/042533, having an International Filing Date of Jul. 18, 2017, which claims the benefit of U.S. Provisional Application No. 62/364,155 filed on Jul. 19, 2016. The disclosures of the prior applications are considered part of and are incorporated by reference in the disclosure of this application.

BACKGROUND

1. Technical Field

This document relates to systems and methods for measuring cardiac output and stroke volume. For example, this document relates to cuff occlusion devices and methods for their use so that cardiac output can be estimated in a non-invasive fashion.

2. Background Information

Cardiac output (CO) is the volume of blood pumped by the heart per minute (e.g., ml blood/min). Cardiac output is a function of heart rate and stroke volume. The heart rate is simply the number of heart beats per minute. The stroke volume is the volume of blood pumped out of the heart with each beat.

Sufficient CO is an essential component in maintaining the metabolic homeostasis of peripheral organs. CO determines the amount of blood available for delivery to working muscle, directly influences performance and therefore is of interest in exercise physiology. Peak exercise CO serves as a powerful prognostic marker in heart failure (HF) and repeated invasive measurement of CO is currently a part of diagnostic testing in advanced HF.

Non-invasive assessment of CO as a basic hemodynamic parameter has been of interest in sport medicine, cardiology and anesthesiology. Non-invasive techniques available are either difficult to use out of health care facilities and technically challenging or less accurate. Indeed, since the Fick principle was introduced in 1870, an accurate method for estimating CO while avoiding blood sampling has been sought. Yet, most methods require sophisticated non-portable equipment, expensive equipment, technical expertise, and/or subject cooperation.

SUMMARY

This document provides systems for measuring cardiac output (and stroke volume) and methods for their use. For example, this document relates to cuff occlusion devices and methods for their use so that cardiac output and stroke volume can be estimated in a non-invasive fashion.

In one aspect, this disclosure is directed to method of measuring a cardiac output of a patient. The method includes: (a) occluding, using an inflatable cuff device for a period of time, a brachial artery of the patient; (b) detecting, using the inflatable cuff while the brachial artery is occluded, a heart rate and a plurality of blood pressure pulse wave measurement curves; (c) determining an average blood pressure pulse wave measurement curve of the plurality of blood pressure pulse wave measurement curves; (d) determining an area under the average blood pressure pulse wave measurement curve; (e) determining a maximal blood pressure of the average blood pressure pulse wave measurement curve; and (f) determining the cardiac output of the patient. The cardiac output equals the heart rate multiplied by the area under the average blood pressure pulse wave measurement curve and divided by the maximal blood pressure of the average blood pressure pulse wave measurement curve.

Such a method of measuring a cardiac output of a patient may optionally include one or more of the following features. The occluding may include pressurizing the inflatable cuff device to an inflation pressure that is at least 30 mmHg above a systolic pressure of the patient. The period of time may be at least 15 seconds. The plurality of blood pressure pulse wave measurement curves may be detected by sensing pressure changes of a fluid used to inflate the inflatable cuff device. The plurality of blood pressure pulse wave measurement curves may be detected by a sensor coupled to the inflatable cuff. The method may also include, prior to said determining the average blood pressure pulse wave measurement curve, eliminating one or more of the blood pressure pulse wave measurement curves. The eliminating the one or more of the blood pressure pulse wave measurement curves may include identifying artifacts in the one or more of the blood pressure pulse wave measurement curves.

In another aspect, this disclosure is directed to a system for measuring cardiac output of a patient. The system includes an inflatable cuff configured for occluding a brachial artery of the patient, a sensor coupled to the inflatable cuff and configured for detecting blood pressure pulse wave measurement curves of the brachial artery, and a controller device. The controller device is configured for: (i) detecting, using the sensor while the brachial artery is occluded, a heart rate and a plurality of blood pressure pulse wave measurement curves; (ii) determining an average blood pressure pulse wave measurement curve of the plurality of blood pressure pulse wave measurement curves; (iii) determining an area under the average blood pressure pulse wave measurement curve; (iv) determining a maximal blood pressure of the average blood pressure pulse wave measurement curve; and (v) determining the cardiac output of the patient, wherein the cardiac output equals the heart rate multiplied by the area under the average blood pressure pulse wave measurement curve and divided by the maximal blood pressure of the average blood pressure pulse wave measurement curve.

Such a method may optionally include one or more of the following features. The sensor may be directly coupled to the inflatable cuff. The sensor may be directly coupled to the controller device. The controller device may be configured for supplying an inflation fluid to the inflatable cuff. The controller device may be configured for outputting the cardiac output on a user interface of the controller device. The controller device may be configured for filtering data of the plurality of blood pressure pulse wave measurement curves. The controller device may be configured for allowing an operator to manually filter data of the plurality of blood pressure pulse wave measurement curves. The sensor may be configured for detecting a heart rate.

In another aspect, this disclosure is directed to a method of measuring a stroke volume of a patient. The method includes: (1) occluding, using an inflatable cuff device for a period of time, a brachial artery of the patient; (2) detecting, using the inflatable cuff while the brachial artery is occluded, a blood pressure pulse wave measurement curve; (3) determining an area under the blood pressure pulse wave measurement curve; (4) determining a maximal blood pressure of the blood pressure pulse wave measurement curve; and (5) determining the stroke volume of the patient. The stroke volume equals the area under the blood pressure pulse wave measurement curve divided by the maximal blood pressure of the blood pressure pulse wave measurement curve.

Particular embodiments of the subject matter described in this document can be implemented to realize one or more of the following advantages. In some embodiments, the devices and methods provided herein are convenient to operate. That is, the level of training and experience required to operate the systems is advantageously not extensive. Additionally, in some embodiments the systems are essentially portable. Therefore the systems can be available for use in various contexts of the hospital, clinic, rehabilitation facility, and the like. Moreover, in some embodiments provided herein CO can be accurately estimated in a minimally invasive fashion using the devices and methods. Such minimally invasive techniques can tend to reduce patient discomfort, recovery times and risks, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims. While this specification contains many specific implementation details, these should not be construed as limitations on the scope of any invention or of what may be claimed, but rather as descriptions of features that may be specific to particular embodiments of particular inventions.

DESCRIPTION OF THE DRAWINGS

Like reference numbers represent corresponding parts throughout.

DETAILED DESCRIPTION

Non-invasive systems for accurately estimating cardiac output (CO) can be fashioned and operated in accordance with the descriptions and concepts provided herein. For example, this document describes cuff occlusion systems and methods for their use so that a patient's cardiac output can be estimated in a non-invasive manner from the patient's perspective.

In one implementation, a patient's brachial artery is occluded by an inflatable cuff device for a period of time. A plurality of blood pressure pulse wave measurement curves are measured by a sensor of the cuff device. The data of the blood pressure pulse wave measurement curves can be used to calculate an estimate of the patient's cardiac output as described further below.

Since the cuff occlusion method provided herein yields a clean and accurate arterial pressure curve, this approach can be advantageously used to quantify CO at rest and/or during exercise. The non-invasive blood pressure (BP) curve detected using this method is well correlated with the invasive aortic BP curve. In addition, the cuff occlusion technique has advantages over the volume-clamp method in its technical simplicity and the ability to apply less complex equations for stroke volume. The cuff occlusion technique provided herein compares closely with conventional method for determining CO (the open circuit acetylene (OpCirc) method) at rest and during exercise.

The principles of the cuff occlusion method provided herein lies in using an inflatable arm cuff as a pressure sensor in special conditions. When the arm cuff is pressurized above systolic blood pressure, it occludes brachial artery and disables the blood flow distally from cuff. By creating this no-flow condition, a small diaphragm develops in the brachial artery at the level of the upper edge of the over-pressurized cuff. As the central pressure changes, pressure waves reach the virtual diaphragm and cause a beat on the membrane like a drumstick. This cause small volume/pressure changes in the cuff because the upper arm tissues are practically incompressible. The pressure changes are recorded by the sensor of the device. In this set-up the local influence of the characteristics of the brachial artery wall is practically eliminated, due to the fact that the arterial wall doesn't move beneath the cuff, and so the received curves are pure pressure waves, essentially identical to those measured invasively.

Figure 1:
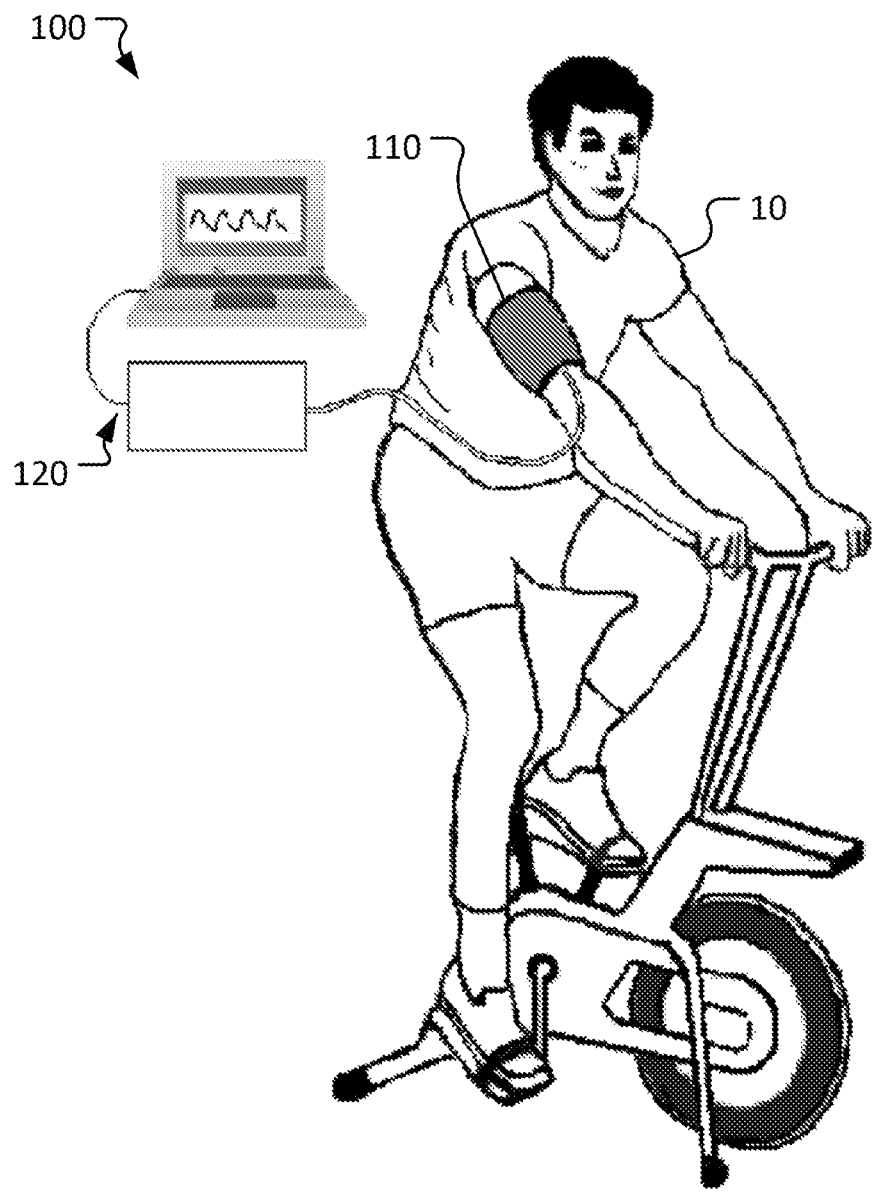
FIG. 1 is an illustration of a patient undergoing a cuff occlusion technique for determining the patient's CO, in accordance with some embodiments.

Referring to FIG. 1, a patient 10 is depicted as undergoing a cuff occlusion procedure for determining the patient's CO. A cuff occlusion system 100 in accordance with some embodiments is used to non-invasively collect data from patient 10, and to use the data to determine an estimate of the CO of patient 10. Cuff occlusion system 100 includes an inflatable cuff 110 and a cuff occlusion controller 120.

Inflatable cuff 110 can be releasably wrapped around an arm of patient 10, and thereafter inflated. Inflatable cuff 110 can be configured and operable to occlude a brachial artery of patient 10 when inflatable cuff 110 is fully inflated. In some cases, one or more other arteries of patient 10 can be occluded without departing from the context of this disclosure. In some embodiments, inflatable cuff 110 is fashioned similarly to a blood pressure cuff.

In the depicted embodiment, cuff occlusion controller 120 is in communication with inflatable cuff 110. In particular, cuff occlusion controller 120 can be in electrical and/or fluidic communication with inflatable cuff 110. In some embodiments, cuff occlusion controller 120 includes a pump and valves that are used to control the inflation of inflatable cuff 110.

In some embodiments, a sensor is coupled to inflatable cuff 110. The sensor is configured for detecting hemodynamic parameters such as, but not limited to, heart rate and blood pressure pulse wave measurement curves from the brachial artery of patient 10. In some embodiments, the sensor is coupled directly to inflatable cuff 110. In some embodiments, the sensor is disposed within cuff occlusion controller 120 while being in communication with inflatable cuff 110. Data collected by the sensor is input to cuff occlusion controller 120. As described further below, cuff occlusion controller 120 is programmed to manipulate the data and to calculate an estimated CO of patient 10.

Figure 2:
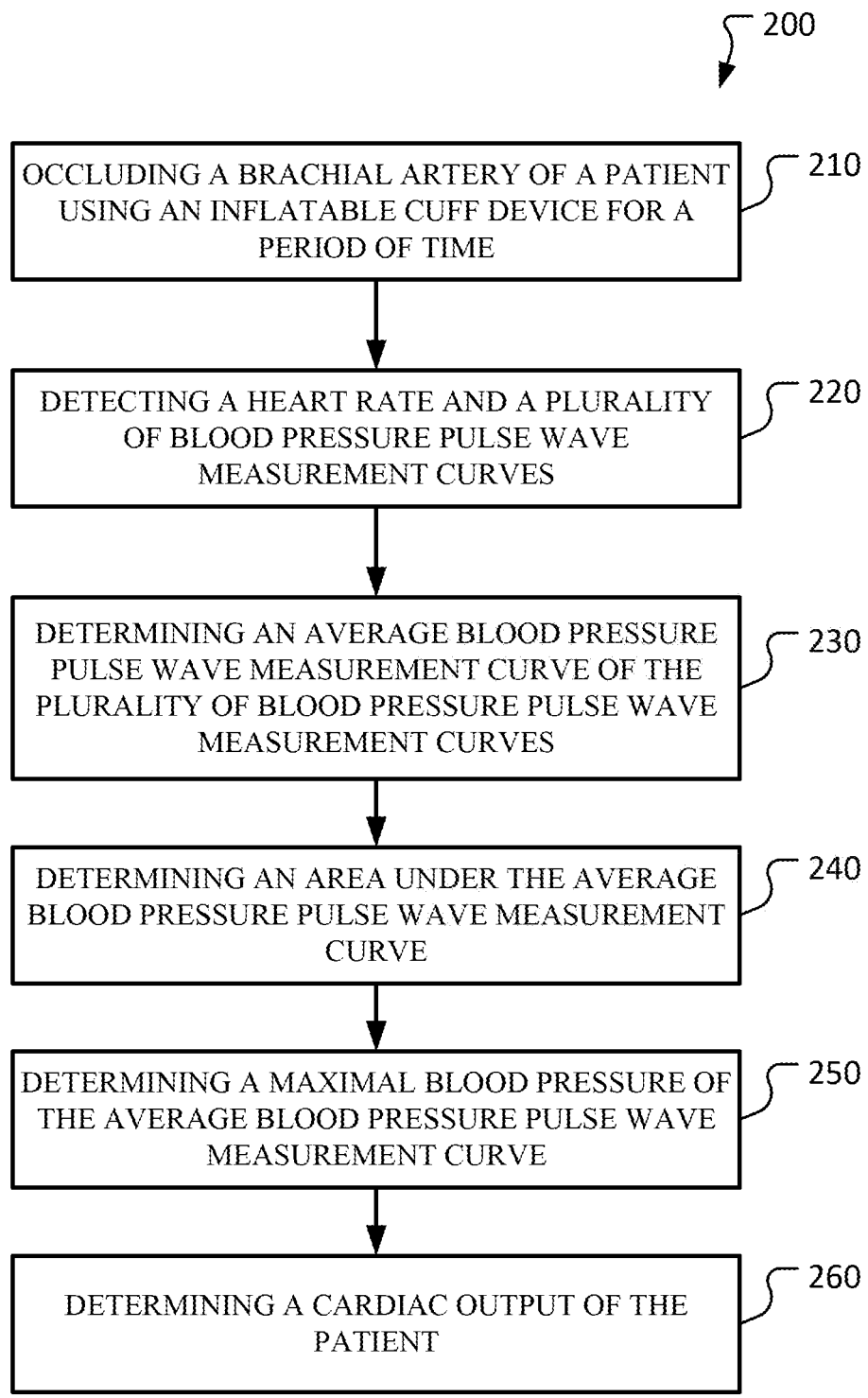
FIG. 2 is a flowchart of a method for performing a cuff occlusion technique for determining a patient's CO, in accordance with some embodiments.

Referring also to FIG. 2, a flowchart depicts a method 200 of measuring a cardiac output of a patient. As described further below, in some cases method 200 can utilize cuff occlusion system 100 as described herein. It should be understood that method 200 is merely one non-limiting example of how the inventive concepts for non-invasively estimating CO provided herein can be implemented.

At step 210, an inflatable cuff device is used to occlude a brachial artery of the patient for a period of time. For example, in the context of cuff occlusion system 100, cuff 110 can be wrapped around the arm of patient 10 and inflated using cuff occlusion controller 120, or manually inflated. When fully inflated, cuff 110 will occlude the brachial artery of patient 10. In some cases, cuff 110 will be used to occlude the brachial artery for a period of time, without limitation, of between about 10 seconds and 30 seconds, or about 15 seconds and 25 seconds, or about 20 seconds and 30 seconds, or about 25 seconds and 35 seconds. In some cases, step 210 is repeated multiple times prior to proceeding to step 220.

At step 220, parameters such as, but not limited to, a heart rate and a plurality of blood pressure pulse wave measurement curves are detected. These data can be detected while the brachial artery is occluded during step 210. In some cases, the sensor coupled to inflatable cuff 110 is used to detect the data. The data can be received and stored in memory by cuff occlusion controller 120.

At step 230, an average blood pressure pulse wave measurement curve of the plurality of blood pressure pulse wave measurement curves is determined. For example, in some embodiments cuff occlusion controller 120 can determine the average blood pressure pulse wave measurement curve based on the data detected at step 220. In some cases, the data from step 220 is filtered prior to performing step 230. For example, in some cases some data that may have artifact or other types of measurement errors or inaccuracies that would tend to decrease the accuracy of method 200 are eliminated from further calculations. Such data may be manually and/or automatically filtered out from being used in step 230.

At step 240, an area under the average blood pressure pulse wave measurement curve can be determined. For example, in some embodiments cuff occlusion controller 120 can determine the area under the average blood pressure pulse wave measurement curve.

At step 250, a maximal blood pressure of the average blood pressure pulse wave measurement curve can be determined. For example, in some embodiments cuff occlusion controller 120 can determine the maximal blood pressure of the average blood pressure pulse wave measurement curve.

At step 260, a cardiac output of the patient can be determined. For example, in some embodiments cuff occlusion controller 120 can determine the cardiac output of the patient. Results from prior steps of method 200 can be used to determine the cardiac output of the patient. In some cases, the following formula can be used to determine the cardiac output of the patient in step 260:

$$CO\left(\frac{1}{\min}\right) = HR\left(\frac{\text{beat}}{\min}\right) \times \frac{AUC}{\text{MaximalPeak}_{amp}}\left(\frac{1}{\text{beat}}\right)$$

where "HR" is the heart rate detected in step 220, "AUC" is the area under the average blood pressure pulse wave measurement curve determined in step 240, and "MaximalPeak$_{amp}$" is the maximal blood pressure of the average blood pressure pulse wave measurement curve determined in step 250.

In another embodiment, the stroke volume (for a single beat of the patient's heart) can be estimated using similar techniques. Whereas, determining the cardiac output using method 200 involves averaging several pressure pulse wave measurement curves, the stroke volume of a single heart beat can be estimated using the AUC of an individual pressure pulse wave curve divided by the amplitude (maximal peak) of that single pressure pulse wave curve.

Examples

Subjects participated in one submaximal exercise study. Cardiac output measurements were performed simultaneously using the brachial occlusion cuff method and the OpCirc method. All measurements were carried out in upright position. At baseline, participants were seated on the up right cycle ergometer Corival, type 906902 V 1.01 (Lode B.V. Medical Technology Groningen, Netherlands). For gas analysis, the Marquette 1100 (The Mass Spectrometer Experts, St. Louis, Mo., U.S.A.) integrated with Medical Graphics CPXD (Medical Graphics Corporation, St. Paul, Minn., U.S.A) was used. Subjects breathed on a mouthpiece only during the time of CO measurement. A single inflatable arm cuff with size based on the arm circumference with 5 cm of overlap (3 cm above cubital fossa) was wrapped around the left arm over brachial artery (cuff identical to standard OMRON CM2 cuff) and connected to the prototype BP monitor developed at Czech Technical University in Prague, Czech Republic. After three minutes of rest, a systemic arterial blood pressure was measured by an auscultatory method. Then, CO and standard BP measurements (accordingly to BHS evaluation protocol for oscillometric blood pressure measurement devices) were assessed twice within 2-4 minutes to allow a complete inert-gas washout from the lungs. Consequently, based on the estimated fitness of each participant, a submaximal protocol consisting of three levels of exercise intensity was performed for four minutes at each level. Measurements of CO were made using both methods simultaneously at minutes three and four at each stage of exercise resulting in a total of eight CO measurements (including rest) for each participant, along with the BP assessed at the end of the last stage. During the data acquisition periods, subjects were encouraged to remain still, breathe in a regular rhythm, avoid coughing or swallowing, take partial breaths, and fully relax the left arm in order to minimize any muscle activity, if possible.

Each measurement with the cuff method consisted of the following steps: the cuff was pressurized to 190 mmHg for 20 seconds and raw BP curve data were recorded on a prototype BP monitor. Measured values were continuously stored in the memory of the device at sampling rate Fs=400 Hz. No other filtering was used during hardware measurement phase. Semi-automatic signal post-processing was performed as follows. Stored signals were filtered to reduce high frequency noise (Butterworth filter of $2^{nd}$ order with cut off frequency 50 Hz). A trained operator selected the beats which were not influenced by artifacts with characteristic pattern. This indicates that all beats with disrupted non-physiological pattern of BP curve or beats, where strong baseline wander due to movement or breathing artifacts was present were not included for analysis. Only subjects with normal sinus rhythm were analyzed; atrial fibrillation, premature ventricle contractions, premature atrial contractions were excluded (circa <20% of beats were considered artifacts). To estimate CO, on average 12, but not less than 8 beats selected from 20 seconds record were considered for further analysis. Average BP beat curve was calculated automatically and consequently heart rate (HR), systolic area under the curve (AUC) and amplitude of maximal peak (MaximalPeak$_{amp}$) were determined automatically. The CO was calculated using the equation [1] based on calculated BP features and stroke volume quantification.

Cardiac output estimate [1]:

$$CO\left(\frac{1}{\min}\right) = HR\left(\frac{\text{beat}}{\min}\right) \times \frac{AUC}{\text{MaximalPeak}_{amp}}\left(\frac{1}{\text{beat}}\right)$$

Figure 3:
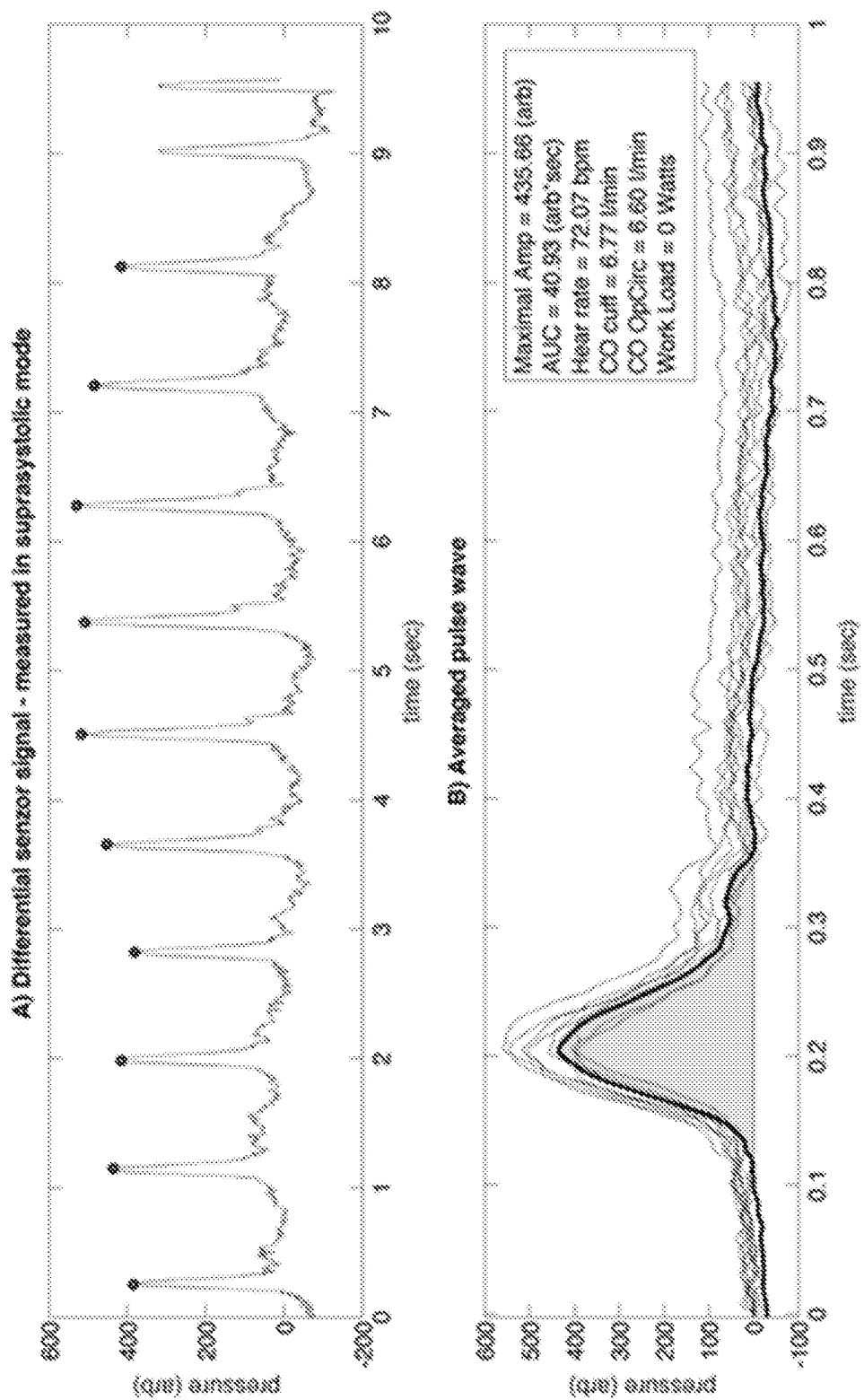
FIG. 3 shows data collected using the cuff occlusion technique from a patient at rest.

FIG. 3 shows example data collected using the non-invasive single cuff method at rest. Raw signal (upper panel A) was analyzed and only beats with good signal quality were selected (those indicated by the dots). The average beat curve was calculated (lower panel B) from the selected beats and heart rate. The area under the curve (AUC) and maximal peak amplitude (Maximal Amp) were determined. Cardiac output was then calculated based on equation [1] (below). CO cuff=cardiac output assessed by the cuff method. CO OpCirc=cardiac output assessed by the comparative Acetylene washing method.

Figure 4:
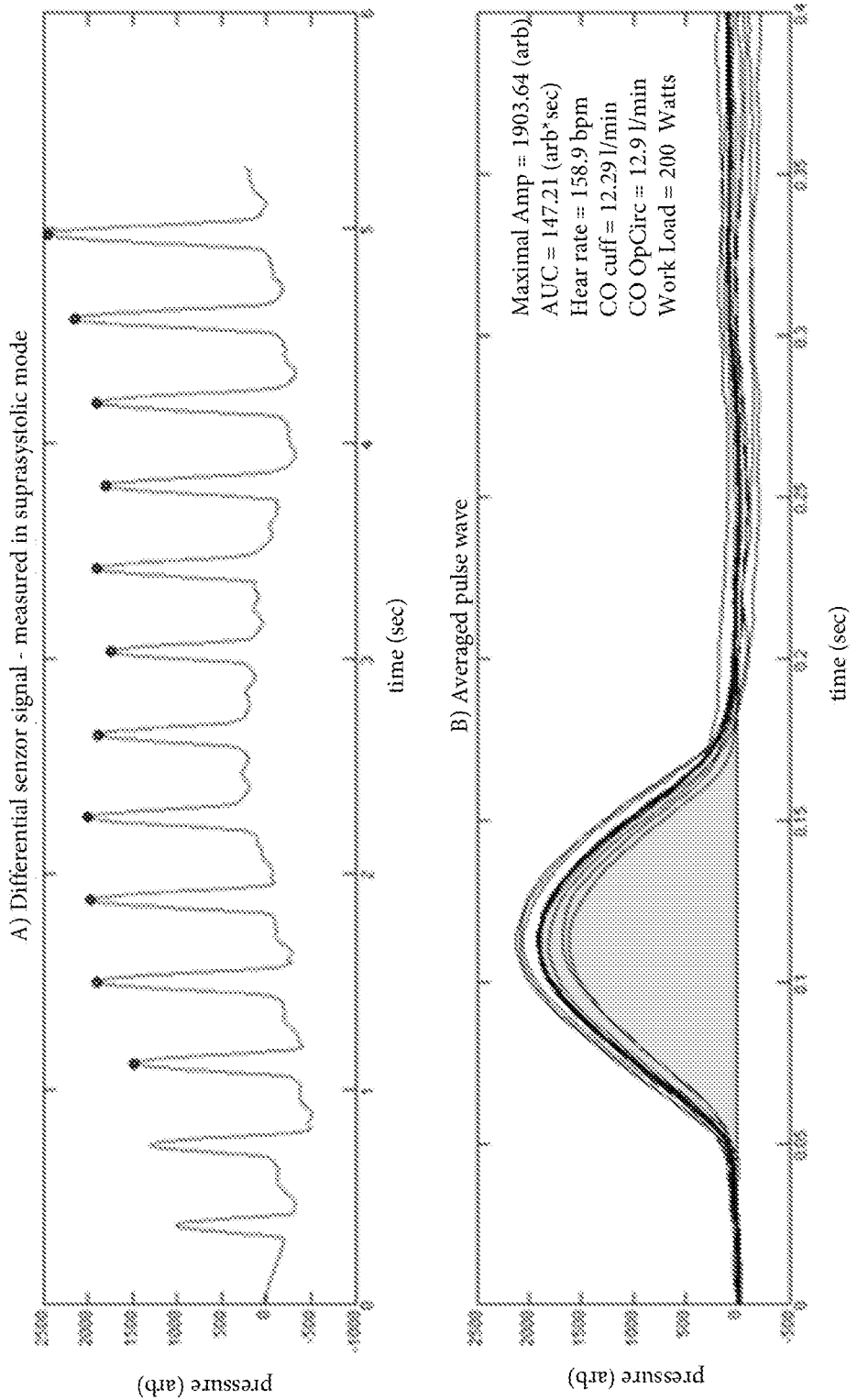
FIG. 4 shows data collected using the cuff occlusion technique from a patient at after exercise.

FIG. 4 shows example data collected using the non-invasive single cuff method during exercise. Raw signal (upper panel A) was analyzed and only beats with good signal quality were selected (those indicated by the dots). The average beat curve was calculated (lower panel B) from the selected beats and heart rate. The area under the curve (AUC) and maximal peak amplitude (Maximal Amp) were determined. Cardiac output was then calculated based on equation [1] (below). CO cuff=cardiac output assessed by the cuff method. CO OpCirc=cardiac output assessed by the comparative Acetylene washing method.

Figure 5:
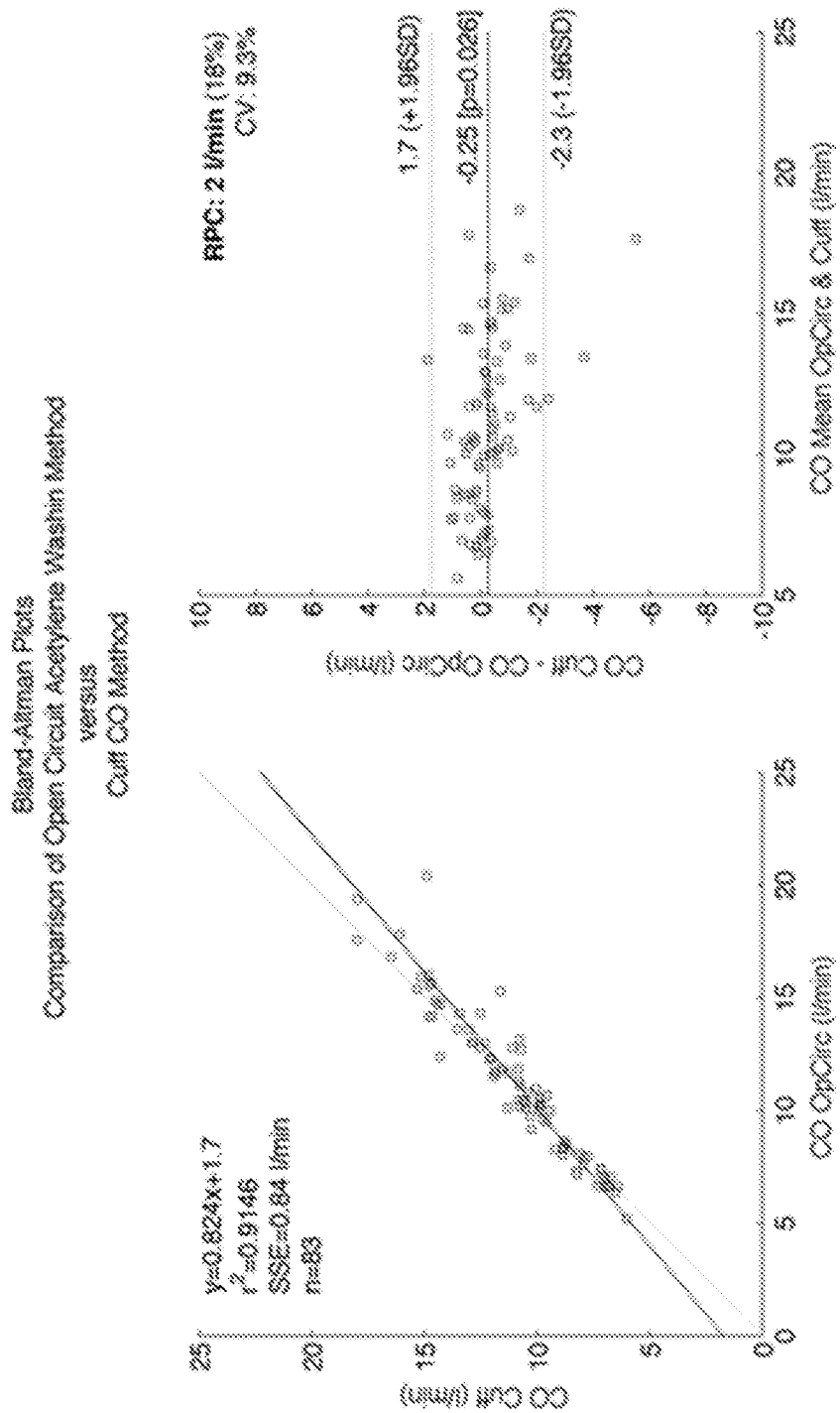
FIG. 5 shows a comparison of data from the cuff occlusion technique to data from the open circuit acetylene (OpCirc) technique.

Data Analysis and Statistical Approach:

Data are shown as mean±standard deviation (SD) unless otherwise specified. The adapted OpCirc data analysis was performed. The BP cuff method measurement analysis methods are described above. As shown in FIG. 5, to test the agreement of both methods, a Bland-Altman (B-A) analysis was utilized. RPC is a reproducibility coefficient, computed as the mean bias±1.96 times its standard deviation. The results are presented as a mean difference with standard deviation, supported by 95% limits of agreement between the methods. Pearson's product-moment correlation coefficients were calculated to evaluate co-variation of methods.

Results:

Six male subjects and seven female subjects were tested. One female subject was excluded due to low quality signal burdened by movement artefacts of arm causing unreadable results of cuff method. Data from a total number of 12 healthy subjects (age 27.6±5.4 years, 50% male, BMI 24.5±3.3) were analyzed. Based on the estimated fitness level of individuals; five males and two females followed exercise protocol consisting of 100, 150 and 200 watts power loads. One male and three females followed a protocol consisting of 50, 100 and 150 watts. One female with a history of a sedentary lifestyle and no sports activities underwent exercise at 50, 100, and 120 watts.

Average error of experimental technique compared to OpCirc was −0.25±1.02 l/min and Pearson's correlation coefficient of 0.96 (rest+exercise), and 0.21±0.42 l/min with Pearson's correlation coefficient of 0.87 (rest only). The B-A analysis (FIG. 5) shows and supports the agreement of the methods within (95% boundaries) 1.7/−2.3 l/min (Bland-Altman coefficients of reproducibility RPC 2 l/min) and $r^2$=0.92 in resting and exercise 1/−0.62 l/min (RPC 0.84 l/min) and $r^2$=0.75 in resting respectively. The B-A analysis for CO lower than 15 l/min improves agreement to 1.4/−1.5 l/min (RPC 1.4 l/min) and $r^2$=0.92.

Figure 6:
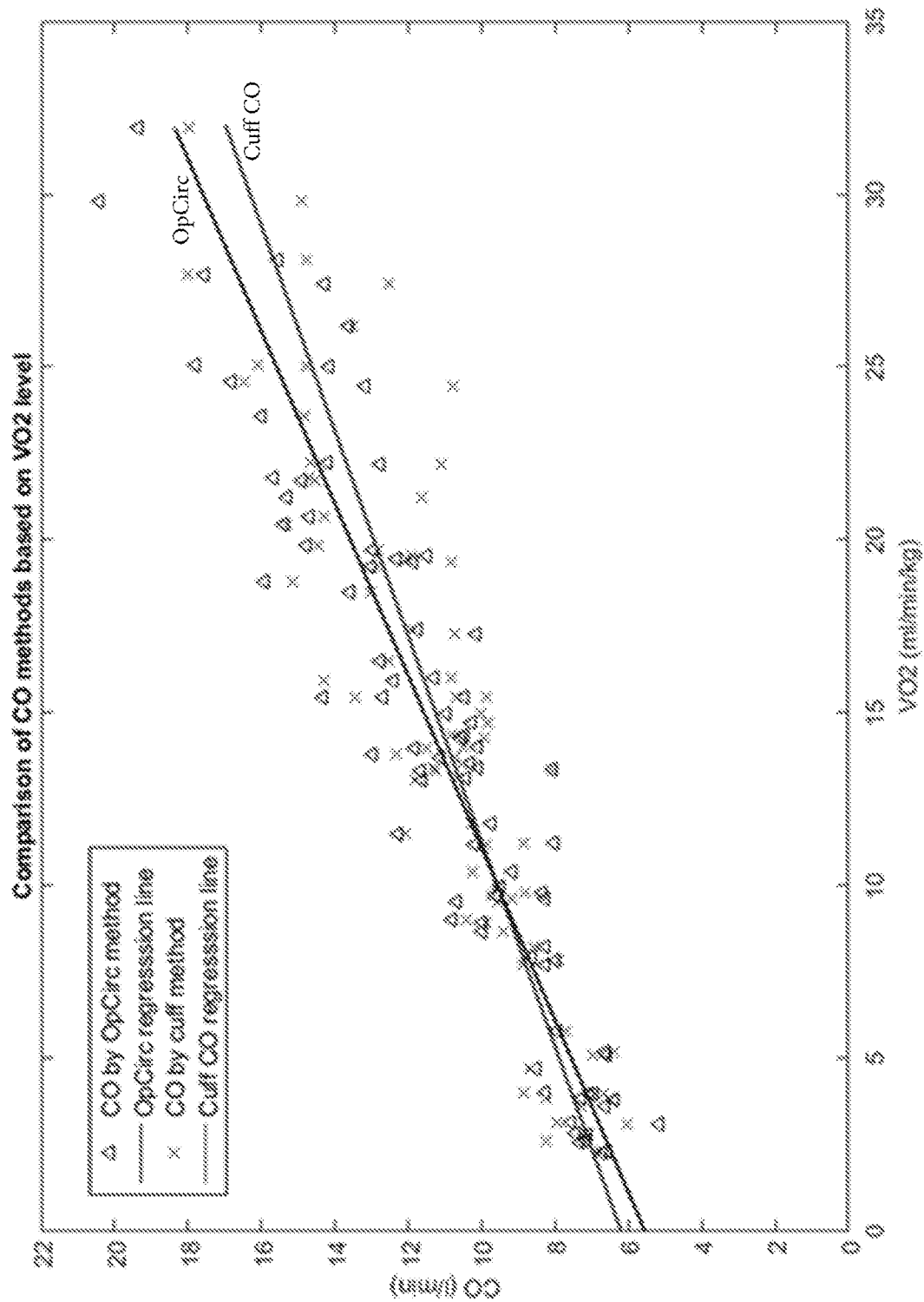
FIG. 6 shows a comparison of data from the cuff occlusion technique to data from the OpCirc technique using $VO_2$ as an independent factor.

FIG. 6 shows a comparison of both methods using $VO_2$ as an independent factor to illustrate the range of aerobic workload we performed the validation of cuff technique. Based on the level of workload, occlusion-cuff method underestimates OpCirc on average up to 4% during exercise, however with narrower standard deviation.

Discussion:

The study was focused on comparing measurements of CO via the non-invasive experimental cuff occlusion method to the validated OpCirc washing technique at rest and during mild to moderate aerobic exercise. For the OpCirc method, conventional computational techniques were used to quantify the uptake of acetylene and to account for changes in lung volume, dead space ventilation, and breath-by-breath variability. The cuff occlusion method was analyzed via semi-automated beat-to-beat pulse pressure wave signal analysis with human supervision. There was a tendency for the experimental cuff occlusion method to underestimate OpCirc at the higher work intensities by up to 4% of measured CO, although the cuff method shows lower variability during exercise.

As stated previously, assessments of CO from the arterial pressure curve have been studied. Hypothetically, if the vascular system doesn't transmit any reflected pressure waves, the flow and pressure curve would be identical, if measured at the same place. The flow/pressure relationship would be defined by peripheral vascular resistance, by analogy to the Ohm's law related to electricity. In vivo, the estimate of ultimate measured flow could be affected by the superimposed reflected pressure waves present as differences in shape of the pressure and the flow curve and thus might influence the accuracy of measurement. Presented experimental data suggests either the negligible effect of reflected waves on the stroke volume calculation in the ejection phase recorded during occluded conditions or that the energy of reflected waves is manifested in the ratio of AUC to the MaximalPeak$_{amp}$.

Another method, known as triangulation, can be used to calculate the stroke volume as well. This approach presumes no flow at the beginning of cardiac cycle, and maximal flow at the pressure amplitude peak with returns to the no flow in times of aortic closure (dicrotic notch). The arterial pressure curve is mostly obtained invasively during catheterization. Although it is possible to estimate CO from this invasive peripheral arterial curve the central aortic pressure curve is typically used for the calculation. In this case, the peripheral arterial pressure curve was obtained through the arm cuff inflated on the suprasystolic pressure (occlusion technique), using the differential pressure sensor showing high correlation with the invasively recorded pressure curve. Thus, this signal can be used for the non-invasive stroke volume estimate. The results demonstrate that CO calculated as an integral of the systolic part of pressure wave measured non-invasively in occlusion at the level of upper brachial artery divided by its maximal amplitude highly correlates with a real blood flow measured by the comparative method. The pressure curve indeed carries information regarding several parameters of the cardiovascular system (BP, blood flow, and peripheral arterial resistance) and the results suggests that the maximal amplitude of the blood pressure wave refer to the actual total peripheral arterial resistance (TPR), if a non-invasive BP signal is recorded in occluded conditions relatively close to the ascendent aorta.

The main practical and physiological difference between occlusion-cuff technique and other methods such as a hybrid of three Windkessel Models including those based on the quantification of wave reflection is that these methods were tested and applied on blood pressure curves obtained mainly invasively (with a free blood flow) in a radial or femoral artery (peripherally), while the BP signal of occlusion-cuff method is obtained non-invasively from a fully occluded brachial artery and from the upper edge of the cuff, which is near the axillar artery and as such, much closer to the central circulation and aortic pressure. Previous studies confirmed high correlation between invasively obtained BP curve from brachial artery (circa 1 cm above the upper edge of inflated cuff) and the non-invasive signal from the cuff. Recording a BP waveform from a fully occluded brachial artery may generate BP waveforms that are morphologically closer to central aortic waveforms to that obtained from a brachial artery in free flow conditions, and thus less affected by peripheral arterial capacitance and ($\tau$).

This experiment has shown that the occlusion-cuff method for CO estimation has strong potential for utilization in heart failure, in intensive care units, in monitoring of patients on hemodialysis, among other disciplines. Simplicity and mobility create the potential for utilization in emergency vehicles, home monitoring of patients, and during research in extreme environments and in exercise physiology. This technique was well tolerated by participants and since the occlusion-cuff technique does not differ from the standard non-invasive BP measurement, except for extended duration of suprasystolic pressure to circa 20 seconds, risks of occlusion-cuff technique should not differ from risks associated with non-invasive BP measurement using the arm cuff.

Data were collected on a sample of healthy subjects in rest and during light to moderate steady-state aerobic exercise. Using a sufficiently tightened arm cuff and motionless arm conditions with relaxed muscles obtains accurate BP signals. Longer time of cuff occlusion (30 seconds) during vigorous exercise can be considered to increase chance of good quality BP recording. Despite higher systemic arterial BP, the occlusion conditions for the data recording can be at least 30 mmHg above SBP to avoid introducing an error.

Conclusion:

Data confirms the feasibility of this novel, non-invasive principle for CO estimate. Contrary to the most similar technique, the volume clamp method, the occlusion technique eliminates the need for technically challenging servo regulated cuff pressure to record the blood pressure curve. Furthermore, pressure signal obtained from brachial artery might be less likely impacted by peripheral vasoconstriction, which built the potential to develop this principle in to an easy to operate, accurate and mobile technique.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of measuring a cardiac output of a patient, the method comprising:
    occluding, using an inflatable cuff device for a period of time, a brachial artery of the patient;
    detecting, using the inflatable cuff while the brachial artery is occluded, a heart rate and a plurality of blood pressure pulse wave measurement curves;
    determining an average blood pressure pulse wave measurement curve of the plurality of blood pressure pulse wave measurement curves;
    determining an area under the average blood pressure pulse wave measurement curve;
    determining a maximal blood pressure of the average blood pressure pulse wave measurement curve; and
    determining the cardiac output of the patient, wherein the cardiac output equals the heart rate multiplied by the area under the average blood pressure pulse wave measurement curve and divided by the maximal blood pressure of the average blood pressure pulse wave measurement curve.

2. The method of claim 1, wherein the occluding comprises pressurizing the inflatable cuff device to an inflation pressure that is at least 30 mmHg above a systolic pressure of the patient.

3. The method of claim 1, wherein the period of time is at least 15 seconds.

4. The method of claim 1, wherein the plurality of blood pressure pulse wave measurement curves are detected by sensing pressure changes of a fluid used to inflate the inflatable cuff device.

5. The method of claim 1, wherein the plurality of blood pressure pulse wave measurement curves are detected by a sensor coupled to the inflatable cuff.

6. The method of claim 1, further comprising, prior to said determining the average blood pressure pulse wave measurement curve, eliminating one or more of the blood pressure pulse wave measurement curves.

7. The method of claim 6, wherein said eliminating the one or more of the blood pressure pulse wave measurement curves comprises identifying artifacts in the one or more of the blood pressure pulse wave measurement curves.

8. A system for measuring cardiac output of a patient, the system comprising:
- an inflatable cuff configured for occluding a brachial artery of the patient;
- a sensor coupled to the inflatable cuff and configured for detecting blood pressure pulse wave measurement curves of the brachial artery; and
- a controller device configured for:
  - detecting, using the sensor while the brachial artery is occluded, a heart rate and a plurality of blood pressure pulse wave measurement curves;
  - determining an average blood pressure pulse wave measurement curve of the plurality of blood pressure pulse wave measurement curves;
  - determining an area under the average blood pressure pulse wave measurement curve;
  - determining a maximal blood pressure of the average blood pressure pulse wave measurement curve; and
  - determining the cardiac output of the patient, wherein the cardiac output equals the heart rate multiplied by the area under the average blood pressure pulse wave measurement curve and divided by the maximal blood pressure of the average blood pressure pulse wave measurement curve.

9. The system of claim 8, wherein the sensor is directly coupled to the inflatable cuff.

10. The system of claim 8, wherein the sensor is directly coupled to the controller device.

11. The system of claim 8, wherein the controller device is configured for supplying an inflation fluid to the inflatable cuff.

12. The system of claim 8, wherein the controller device is configured for outputting the cardiac output on a user interface of the controller device.

13. The system of claim 8, wherein the controller device is configured for filtering data of the plurality of blood pressure pulse wave measurement curves.

14. The system of claim 8, wherein the controller device is configured for allowing an operator to manually filter data of the plurality of blood pressure pulse wave measurement curves.

15. A method of measuring a stroke volume of a patient, the method comprising:
- occluding, using an inflatable cuff device for a period of time, a brachial artery of the patient;
- detecting, using the inflatable cuff while the brachial artery is occluded, a blood pressure pulse wave measurement curve;
- determining an area under the blood pressure pulse wave measurement curve;
- determining a maximal blood pressure of the blood pressure pulse wave measurement curve; and
- determining the stroke volume of the patient, wherein the stroke volume equals the area under the blood pressure pulse wave measurement curve divided by the maximal blood pressure of the blood pressure pulse wave measurement curve.

* * * * *